United States Patent

Ohkawa

Patent Number: 5,362,877
Date of Patent: Nov. 8, 1994

[54] PROCESS OF SYNTHESIZING ACETALS

[75] Inventor: Atsuhiro Ohkawa, Kanagawa, Japan

[73] Assignee: Fuji Photo Film Co., Ltd., Kanagawa, Japan

[21] Appl. No.: 64,990

[22] Filed: May 24, 1993

[30] Foreign Application Priority Data

May 25, 1992 [JP] Japan .................................. 4-132707

[51] Int. Cl.$^5$ .................. C07D 211/72; C07D 211/78; C07D 211/68
[52] U.S. Cl. ...................................... 546/290; 546/300
[58] Field of Search ................................. 546/290, 300

[56] References Cited

PUBLICATIONS

07/885359 by Ohkawa et al., filed May 19, 1992.

Primary Examiner—C. Warren Ivy
Assistant Examiner—D. Margaret M. Mach
Attorney, Agent, or Firm—Birch, Stewart, Kolasch & Birch

[57] ABSTRACT

A process of synthetizing an acetal, which comprises reacting, i) a compound represented by formula (I);

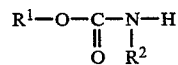

(I)

with ii) at least one compound selected from the group consisting of paraformaldehyde, trioxane and compound represented by formula (II);

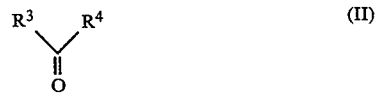

(II)

iii) a compound represented by formula (III);

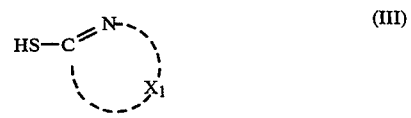

(III)

in the presence of at least one of a Lewis acid and a metal salt to synthesize the acetal represented by formula (IV);

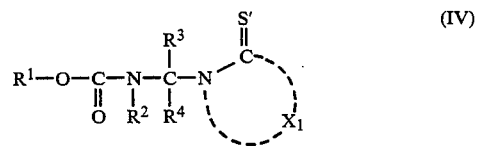

(IV)

wherein $R^1$, $R^2$, $R^3$, $R^4$, and $X_1$ have the same meaning as those in claim (I).

20 Claims, No Drawings

PROCESS OF SYNTHESIZING ACETALS

FIELD OF THE INVENTION

The present invention relates to a process of economically synthesizing a compound having an acetal skeleton useful as photographic couplers or various organic synthesis intermediate products.

BACKGROUND OF THE INVENTION

For the synthesis process of acetals having the following structure:

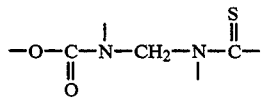

sufficient investigations have not yet been made and as a general process, there is a process described in Japanese Patent Application No. 3-145175 (corresponding to U.S. patent application Ser. No. 885,359 and EP5148-96A). Practically, according to the foregoing process as shown in following Scheme (I), by forming a methylol by the reaction of compound (A) and paraformaldehyde, compound (B) is synthesized and by reacting compound (B) and mercaptoazole in the presence of zinc iodide, desired compound (C) is synthesized.

Scheme (I)

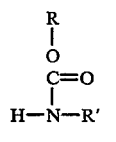 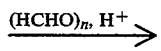

(A)

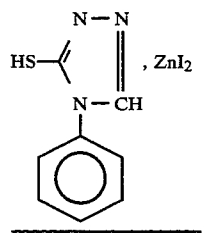

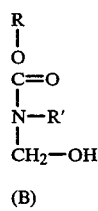

(B)

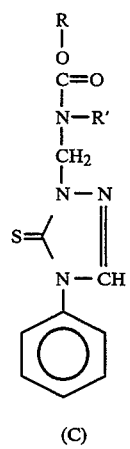

(C)

However, the foregoing process has the following problems, that is, i) 2 steps are required for obtaining the desired product, ii) the yield in each step is low, iii) since the yield for compound (B), which is an intermediate product, is low and the crystallinity thereof is inferior, it is very difficult to isolate the compound (B) by means other than a column purification, iv) furthermore, in the synthesis of compound (B), paraformaldehyde deposits onto a cooling pipe, and v) if the purity of compound (B) is not high, the synthetic reaction of compound (C) can not be carried out well, i.e., the yield of compound (C) is low. For example, in the example for synthesizing the compound in EP 514896A cited above the yield is only 9.6%.

SUMMARY OF THE INVENTION

The object of the present invention is to provide a synthesis process capable of simply and economically synthesizing acetals represented by formula (IV).

It has now been discovered that the aforesaid object can be attained by the present invention described hereinbelow.

According to the present invention, there is provided a process of synthesizing an acetal, which comprises reacting, i) a compound represented by formula (I):

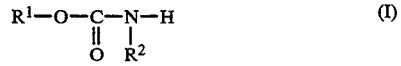

wherein $R^1$ represents an alkyl group, an aryl group, or a heterocyclic group and $R^2$ represents an alkyl group or an aryl group, said groups represented by $R^1$ and $R^2$ may be substituted, ii) at least one compound selected from the group consisting of paraformaldehyde, trioxane and compound represented by formula (II):

wherein $R^3$ and $R^4$ each independently represents a hydrogen atom, an alkyl group, an alkenyl group, an alkinyl group, an alkoxycarbonyl group, an aryloxycarbonyl group, a carbamoyl group, a sulfamoyl group, an aryl group, or a heterocyclic group, said groups represented by $R^3$ and $R^4$ may be substituted, and iii) a compound represented by formula (III):

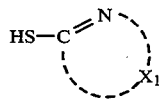
(III)

wherein $X_1$ represents a non-metallic atomic group necessary for forming a 5-membered or 6-membered nitrogen atom-containing heterocyclic group which may be condensed with another ring to form a di- or tri-cyclic group, said group represented by $X_1$ may be substituted, in the presence-of at least one of a Lewis acid and a metal salt to synthesize the acetal represented by formula (IV)

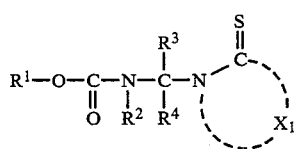
(IV)

wherein $R^1$, $R^2$, $R^3$, $R^4$, and $X_1$ have the same meaning as those of formula (I) to formula (III).

DETAILED DESCRIPTION OF THE INVENTION

In formula (I), $R^1$ represents an alkyl group (the number of carbon atoms is preferably from 1 to 40, more preferably from 1 to 30, and most preferably from 1 to 20 (hereinafter these are simply shown as $C_{1-40}$, $C_{1-30}$ and $C_{1-20}$); e.g., methyl, tert-butyl, 2-ethylhexyl, decyl, octadecyl, and benzyl), an aryl group ($C_{6-24}$, $C_{6-12}$ and $C_6$; e.g., phenyl, 1-naphthyl, and 2-naphthyl), or a heterocyclic group (preferably a 5- or 6-membered heterocyclic group containing at least one of N, O and S atoms as hetero atom, and the heterocyclic ring in the group may be condensed to form di- or tri- condensed ring; e.g., 3-pyridyl, 2-thienyl, and 1-methyl-3-indolyl). Also, these groups each may have at least one substituent and as the substituent, there are an alkyl group and aryl group the same as disclosed above, a carbamoyl group ($C_{1-30}$, $C_{1-20}$ and $C_{1-14}$; e.g., carbamoyl, dimethylcarbamoyl, propylcarbamoyl, octadecylcarbamoyl, and morpholinocarbonyl), an alkoxy group ($C_{1-40}$, $C_{1-30}$ and $C_{1-20}$; e.g., methoxy, tert-butoxy, and tetradecyloxy) , an aryloxy group ($C_{6-24}$, $C_{6-12}$ and $C_6$; e.g. , phenoxy and 2-naphthoxy), an alkylthio group (C1-30, $C_{1-20}$ and $C_{1-12}$; e.g., methylthio, isopropylthio, and decylthio) , an arylthio group ($C_{6-24}$, $C_{6-12}$ and $C_6$; e.g., phenylthio and 1-naphthylthio) , an alkoxycarbonyl group ($C_{2-40}$, $C_{2-30}$ and $C_{2-20}$; e.g., methoxycarbonyl, 2-ethylhexyloxycarbonyl, 2-hexyldecyloxycarbonyl, and isopropyloxycarbonyl), an aryloxycarbonyl group ($C_{7-25}$, $C_{7-13}$ and $C_7$; e.g., phenoxycarbonyl an acyl group ($C_{2-40}$, $C_{2-30}$ and $C_{2-20}$; e.g., acetyl, pivaloyl, and benzoyl; in the present invention an acyl moiety includes an aliphatic and aromatic acyl moiety;), a sulfonyl group ($C_{1-30}$, $C_{1-20}$ and $C_{1-10}$; e.g., methanesulfonyl and p-toluenesulfonyl; in the present invention a sulfonyl moiety includes an alkyl- and arylsulfonyl moiety;), a nitro group, a cyano group, a halogen atom (e.g., fluorine, chlorine, and bromine), a sulfamoyl group ($C_{0-30}$, $C_{0-20}$ and $C_{0-10}$); an acylamino group ($C_{2-40}$, $C_{2-30}$ and $C_{2-20}$; e.g., acetylamino, butanoylamino, and benzoylamino), a sulfonylamino group ($C_{1-40}$, $C_{1-30}$ and $C_{1-20}$) , and an amino group (($C_{0-30}$, $C_{0-20}$ and $C_{0-10}$) e.g., dimethylamino). These substituents may be further substituted with at least one of substituents described above.

Also, $R^2$ represents a substituted or unsubstituted alkyl group ($C_{1-40}$, $C_{1-30}$ and $C_{1-20}$; e.g., methyl, isopropyl, ethyl, hexyl, cyclo-hexyl, tetradecyl, and benzyl ) or a substituted or unsubstituted aryl group ($C_{6-24}$, $C_{6-12}$ and $C_6$; e.g., phenyl, 1-naphthyl, and 2-naphthyl) . The alkyl and aryl groups each may be substituted with at least one substituent as illustrated above as the substituent for the groups shown by $R^1$.

In formula (II) , $R^3$ and $R^4$ each independently represents a hydrogen atom, an alkyl group ($C_{1-20}$, $C_{1-10}$ and $C_{1-5}$), an alkenyl group ($C_{2-20}$, $C_{2-10}$ and $C_{2-5}$), an alkinyl group ($C_{2-20}$, $C_{2-10}$ and $C_{2-5}$), an alkoxycarbonyl group ($C_{2-20}$, $C_{2-10}$ and $C_{2-6}$) , an aryloxycarbonyl group ($C_{7-11}$ and $C_7$), a carbamoyl group ($C_{1-20}$, $C_{1-10}$ and $C_{1-5}$), a sulfamoyl group. ($C_{0-20}$, $C_{0-10}$ and $C_{0-5}$), and an aryl group ($C_{6-12}$ and $C_6$) , or a heterocyclic group (preferably a 5- or 6-membered heterocyclic group containing at least one of N, S and O atoms as hetero atom; the heterocyclic group may be a monocyclic group or a di- or tri- condensed cyclic group; more preferably the heterocyclic group is a mono- or di- cyclic group and most preferably a monocyclic group). As the aryl group, there are phenyl, naphthyl, etc., and as the heterocyclic group, there are 2-furyl, 2-thienyl, etc. Also, other practical examples of the foregoing groups are those described above for the groups shown by $R^1$. When $R^3$ or $R^4$ represents other group than a hydrogen atom, the group may further have at least one of substituents such as those disclosed above as examples for substituents of the groups represented by $R_1$.

$R^3$ and $R^4$ each is preferably a hydrogen atom, an alkyl group having from 1 to 6 carbon atoms, or a phenyl group, more preferably, at least one of $R^3$ and $R^4$ represents a hydrogen atom, and most preferably $R^3$ and $R^4$ each represents a hydrogen atom.

The preferred compounds of ii) are paraformaldehyde and trioxane.

In formula (III), $X_1$ represents a non-metallic atomic group necessary for forming a 5-membered or 6-membered N-containing heterocyclic ring, the ring may be condensed with another ring to form a di- or tri- cyclic condensed ring, and also $X_1$ or the condensed ring may have at least one of substituent those disclosed above as examples for substituents of the groups represented by $R_1$. In the heterocyclic ring at least one of N, O, and S atoms may be further contained.

The preferred structures of the mercapto nitrogen-containing heterocyclic moiety of the compound represented by formula (III) are those shown by following formulae (III-1) to (III-8). In the formulae (III-1) to (III-8), the bonding(s) represents the bonding position to a hydrogen atom or a substituent.

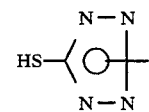
(III-1)

-continued

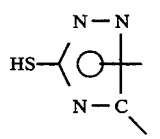 (III-2)

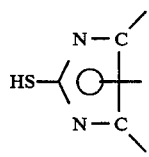 (III-3)

(III-4)

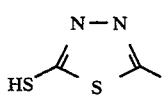 (III-5)

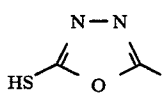 (III-6)

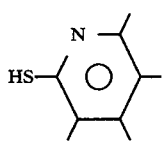 (III-7)

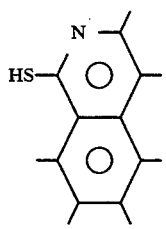 (III-8)

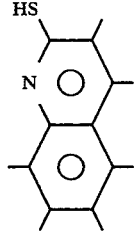

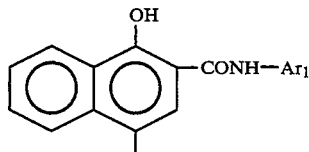 (V)

wherein Ar₁ represents a substituted or unsubstituted alkyl or aryl group.

Preferred alkyl and aryl groups and substituted groups thereof are the same as the definition for the substituents for the group represented by $R^1$ in formula (I).

Examples of an alkyl group include a methyl group, a propyl group, a butyl group, a decyl group, a 2-hexyldecyl group, an octadecyl group, an isobutyl group and 1,1-dimethylpropyl group, and examples of an aryl group include a phenyl group, a 1-naphthyl group and 2-naphthyl group. These groups may further have at least one of the above-described substituents exemplified for $R^1$.

As the Lewis acid and the metal salt being used in the present invention, there are trivalent boron compounds [e.g., $BF_3$, $BF_3OEt_2$, $BCl_3$, $BBr_3$, and $B(OCH_3)_3$], trivalent aluminum compounds (e.g., $AlCl_3$ and $AlBr_3$), divalent nickel compounds (e.g., $NiCl_2$), divalent zinc compounds (e.g., $ZnCl_2$, $ZnBr_2$, and $ZnI_2$), tetravalent or heptavalent vanadium compounds (e.g., $VOCl_2$ and $VCl_5$), monovalent or divalent silver compounds (e.g., AgCl and $AgCl_2$), iodotrimethylsilane, monovalent or divalent copper compounds (e.g., $CuBr_2$, $CuCl_2$, $CuSO_4$, CuI, and CuCl), and solid acid catalysts.

In these compounds, the boron compounds ($BF_3$, $BF_3OEt_2$, $BCl_3$, $BBr_3$, $B(OCH_3)_3$, etc.), the zinc compounds ($ZnCl_2$, $ZnBr_2$, $ZnI_2$, etc.), and the copper compounds ($CuBr_2$, $CuCl_2$, $CuSO_4$, etc.) are preferred and $BF_3$ or the ether complexes thereof, $BCl_3$, and the divalent copper salts (e.g., $CuBr_2$ and $CuCl_2$) are particularly preferred.

These reagents may be used solely or as a mixture of them, or further a halogen ion source such as LiBr, LiCl, LiI, NaCl, NaBr, NaI, KBr, KI, HCl, HBr, etc., may be added to these reagents. Furthermore, the metal salt may be formed in the reaction system by a method of reacting a metal oxide (CuO, ZnO, etc.) or a metal hydroxide ($Cu(OH)_2$, $Zn(OH)_2$, etc.) and a protonic acid (HBr, HCl, $H_2SO_4$, etc.) in the system.

The Lewis acid, the metal compound and the halogen ion source may be added into the reaction system at any form, for example, as a solid or as a liquid such as $BF_3O$-$Et_2$, and when it is a gas it may be used after dissolving it into a solvent.

A dehydrating agent such as a molecular sieve, magnesium sulfate, calcium chloride, etc., may exist in the system.

As the mol ratio of the compounds for the reaction, each of the compounds of i), ii) and iii) may be used in an equimolar amount. Also, for accelerating the reaction, any one of these compounds may be used in excess and in this case, the excess amount of the compound is preferably within 10 times, and more preferably within twice the smallest molar amount of these compounds of i), ii) and iii).

The Lewis acid or the metal salt can be used in a molar amount of from 0.001 times to 10 times the small- In these structures, the structures shown by formulae (III-1), (III-2), (III-4), (III-5), and (III-6) are more preferable and the structures shown by formulae (III-1) and (III-4) are particularly preferable.

As the substituent of the heterocyclic group or the condensed ring of formulae (III-1) to (III-8), there are the substituents described above as the substituents for the groups shown by $R^1$ in formula (I). These groups may further have at least one of the substituents described above.

Examples of the preferred substituent are an alkyl group (e.g., ethyl, butyl, tert-butyl, and benzyl), an aryl group (e.g., phenyl), an alkylthio group, an alkoxycarbonyl group, and an aryloxycarbonyl group.

A preferred example of $R^1$ in formulae (I) and (IV) is a group represented by formula (V):

est molar amount of the three compounds of i), ii) and iii).

The optimum amount of the Lewis acid or the metal salt other than copper compounds depends upon the kind of the Lewis acid or the metal salt but is preferably used in the range of from 0.1 times to 5 times the smallest molar amount of the foregoing compounds. Also, the optimum amount of the copper compound is preferably used in the range of from 0.005 times to 0.5 times from the economical and environmental view points.

The molar amount of the halogen source is 0.001 times to 20 times the smallest molar amount of the compounds i), ii) and iii).

The reaction of the three kinds of the compounds is usually carried out at a temperature of from 0° C. to 150° C., preferably from 15° C. to 100° C., and particularly preferably from 20° C. to 80° C.

As the reaction solvent, various solvents can be used but hydrocarbon solvents (benzene, toluene, hexane, etc.), halide solvents (methylene chloride, chloroform, chlorobenzene, 1,2-dichloroethane, etc.), ether solvents (tetrahydrofuran, anisole, etc.), and non-protonic polar solvents (acetonitrile, nitromethane, dimethyl sulfoxide, N,N'-dimethylimidazolidinone, N,N-dimethylformamide, etc.) are preferably used. Also, plural solvents may be used as a mixture thereof and further the reaction may be carried out without using solvent. The reaction mixture can be made in any order so long as all of the three compounds are present in the reaction system. For example, the solvent may be added into a mixture of the three compounds and a metal compound, or after addition of a solvent into a mixture of the three compounds, a Lewis acid may be added into this mixture.

The concentration of the reactant having the smallest concentration in the reaction solvent is preferably at least $10^{-6}$ mol/liter, more preferably at least $10^{-4}$ mol/liter and most preferably at least $10^{-2}$ mol/liter (paraformaldehyde is calculated as HCHO).

The reaction time is in the range of from 30 minutes to 3 days although the reaction time differs largely according to the properties of the reactants. The reaction is usually carried out in the range of from 1 hour to 15 hours, and preferably from 2 hours to 10 hours.

As the post-treatment of the reaction, after the reaction is finished, the reaction mixture is washed with water and then, the organic layer formed is collected and concentrated. The desired product may frequently be isolated by adding a proper solvent to the residue formed. Also, in another method, the purification of the desired product can be carried out by an ordinary treating method such as by distilling the residue obtained by concentrating the organic layer or by carrying out a column chromatographic purification using silica gel.

Practical examples of the compounds represented by formula (IV) and the compounds having $R^1$ represented by formula (V) are illustrated in the following tables but the invention is not limited to these compounds.

TABLE 1

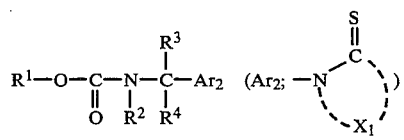

$$R^1-O-\underset{\underset{O}{\|}}{C}-\underset{\underset{R^2}{|}}{N}-\underset{\underset{R^4}{|}}{\overset{\overset{R^3}{|}}{C}}-Ar_2 \quad (Ar_2; -N\underset{X_1}{\overset{\overset{S}{\|}}{\underset{}{C}}})$$

| Compound No. | $R^1$ | $R^2$ | $R^3$ | $R^4$ | $Ar_2$ |
|---|---|---|---|---|---|
| IV-1 | –C₆H₅ | –C₆H₅ | H | H | –N(N=N)C(=S)–N(N=N)–C₆H₅ |
| IV-2 | –C₆H₅ | –CH₂–C₆H₅ | " | " | " |
| IV-3 | –C₆H₅ | –C₆H₁₃ | " | " | " |
| IV-4 | –C₂H₅ | –C₆H₅ | " | " | " |

TABLE 1-continued $$R^1-O-\underset{\underset{O}{\|}}{C}-\underset{\underset{R^2}{|}}{N}-\underset{\underset{R^4}{|}}{\overset{R^3}{C}}-Ar_2 \quad (Ar_2; -N\begin{array}{c}\overset{S}{\|}\\ C\\ \diagdown\\ X_1\end{array})$$

| Compound No. | $R^1$ | $R^2$ | $R^3$ | $R^4$ | $Ar_2$ |
|---|---|---|---|---|---|
| IV-5 | benzyl (C6H5-CH2-) | cyclohexyl | H | H | 1-phenyl-4-thioxo-tetrazol-type ring |
| IV-6 | " | -CHCO2C2H5 with CH3 | H | H | 4-(CH2CO2C3H7)-thioxo-tetrazole |
| IV-7 | " | -CH2CO2C2H5 | H | H | 4-C4H9-thioxo-tetrazole |
| IV-8 | 4-CH3O-C6H4-CH2- | -CH2CH2F | H | H | N-N ring with C(=S), O, C-SCH3 |

TABLE 2

$$\begin{array}{c}\text{naphthol with CONH-Ar}_1\text{ and }\\ O-C(=O)-NH-\underset{\underset{R^4}{|}}{\overset{R^3}{C}}-Ar_2 \quad (Ar_2; -N\begin{array}{c}\overset{S}{\|}\\ C\\ \diagdown\\ X_1\end{array})\end{array}$$

| Compound No. | $Ar_1$ | $R^2$ | $R^3$ | $R^4$ | $Ar_2$ |
|---|---|---|---|---|---|
| VI-1 | 2-methyl-6-OC14H29-phenyl | -CH(CH3)2 | H | H | 1-phenyl-4-thioxo-tetrazole |

TABLE 2-continued
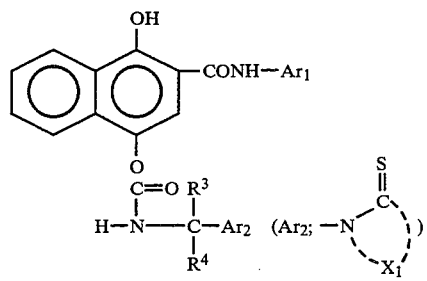
| Compound No. | Ar₁ | R² | R³ | R⁴ | Ar₂ |
|---|---|---|---|---|---|
| VI-2 | " | " | " | " | (1-butyl-tetrazoline-5-thione) |
| VI-3 | " | " | " | " | (N–N thiadiazole with S and SCH₃) |
| VI-4 | " | " | " | " | (1-pyridine-2-thione) |
| VI-5 | " | (phenyl) | " | " | (1-phenyl-tetrazoline-5-thione) |
| VI-6 | (phenyl with OC₁₄H₂₉) | (phenyl with OCH₃) | H | H | (1-phenyl-tetrazoline-5-thione) |
| VI-7 | " | —CH₂CO₂CH₃ | " | " | (1-butyl-tetrazoline-5-thione) |

TABLE 2-continued

[Structure: 1-hydroxy-2-naphthamide with CONH-Ar₁ at position 2 and OC(=O)NH-C(R³)(R⁴)-Ar₂ at position 4, with R² on the carbamate; (Ar₂: N-linked heterocycle with C=S and X₁)]

| Compound No. | Ar₁ | R² | R³ | R⁴ | Ar₂ |
|---|---|---|---|---|---|
| VI-8 | " | —CH₂CH₂Cl | " | " | 1-phenyl-4H-1,2,4-triazoline-5-thione (N–N=N ring with S, N-phenyl) |
| VI-9 | 3-methyl-2-(OC₁₀H₂₁)-naphthyl | —CH₂CO₂C₂H₅ | " | " | 4-butyl-1,3,4-thiadiazoline-2-thione-type ring (N–N=CH, S, N-C₄H₉) |
| VI-10 | —(CH₂)₃OC₁₂H₂₅ | " | " | " | " |
| VI-11 | —(CH₂)₃—O—[2,4-di-t-C₅H₁₁-phenyl] | " | " | " | " |
| VI-12 | —C₁₂H₂₅ | —CH(CH₃)₂ | H | H | 5-[(1-methoxycarbonyl)ethylthio]-1,3,4-thiadiazoline-2-thione |
| VI-13 | 2-methyl-6-(OC₁₄H₂₉)phenyl | " | H | —CO₂CH₃ | 1-phenyl-tetrazoline-5-thione type |
| VI-14 | " | —CH₂CH₂Cl | H | H | 4-butyl-1,3,4-thiadiazoline-2-thione type |

TABLE 2-continued

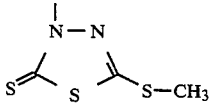

| Compound No. | Ar₁ | R² | R³ | R⁴ | Ar₂ |
|---|---|---|---|---|---|
| VI-15 | " | " | –C₆H₅ (phenyl) | H | " |
| VI-16 | " | " | —CH₃ | —CH₃ | " |
| VI-17 | " | —CH₂CO₂C₂H₅ | H | H | (tetrazole-thione group with S–CH₃) |

The present invention is further explained in detail by referring to the following examples but the invention is not limited to these examples.

EXAMPLE 1

Synthesis of Compound (VI-7) using BF₃OEt₂

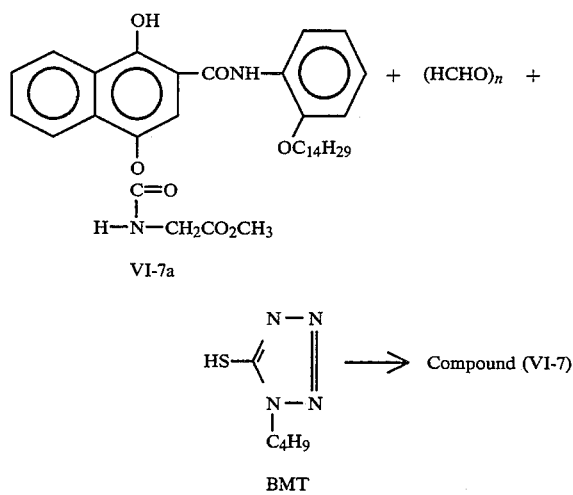

A mixture obtained by mixing simultaneously 2 mmols of Compound (VI-7a), paraformaldehyde (2 mmols as HCHO, and so forth), and 2 mmols of BMT (1-n-butyl-5-mercaptotetrazole) was suspended in 20 ml of 1,2-dichloroethane and then 5 mmols of BF₃OEt₂ was added to the suspension. Then, after carrying out the reaction for 6 hours at 45° C., 20 ml of water and 2 ml of triethanolamine were added to the reaction mixture and the result mixture was-stirred for one hour at room temperature. Thereafter, 5 ml of 2N hydrochloric acid and 30 ml of methylene chloride were added thereto and the organic layer formed was collected and washed twice with 50 ml of water. The organic layer was then dried with anhydrous sodium sulfate, concentrated and the residue formed was purified by silica gel column chromatography to provide 1.22 mmols (yield 61%) of Compound (VI-7). (When the product was recrystallized from ethyl acetatehexane, a product having a melting point of from 78.0° C. to 79.0° C. was obtained. However, when the product was recrystallized from isopropyl alcohol-hexane, the crystal form was changed to give a product having a melting point of 96.0° C. to 97.0° C.)

EXAMPLE 2

Synthesis of Compound (VI-7) using CuBr₂

A mixture composed of 2 mmols of Compound (VI-7a), 2 mmols of paraformaldehyde, 2 mmols of BMT, 0.4 mmol of CuBr₂, and 20 ml of toluene was reacted for 7 hours at 45° C. Thereafter, 5 ml of 2N hydrochloric acid, 30 ml of ethyl acetate, and 30 ml of water were added to the reaction mixture followed by stirring and the aqueous layer formed was collected. The organic layer obtained was washed twice with 30 ml of water, dried with anhydrous sodium sulfate, and treated as in Example 1 to provide 1.48 mmols (yield 74%) of Compound (VI-7).

EXAMPLE 3

Synthesis of Compound (VI-7) using various Lewis acids or metal salts

The same reaction as in Example 2 was followed except that each of the Lewis acids and the metal salts shown in Table 3 below was used in place of CuBr₂.

TABLE 3

| No. | Lewis Acid or Metal Salt[1] | | Yield (%) of Compound (VI-7) |
|---|---|---|---|
| 1 (Invention) | CuCl₂ | (0.4 mmol) | 43% |
| 2 (Invention) | CuO 25% HBr acetic | (0.4 mmol) (0.8 mmol | 72% |

TABLE 3-continued

| No. | Lewis Acid or Metal Salt[1] | | Yield (%) of of Compound (VI-7) |
| --- | --- | --- | --- |
| | acid solution | as HB$_2$) | |
| 3 (Invention) | CuCl$_2$ LiBr | (0.4 mmol) (1.0 mmol) | 62% |
| 4 (Invention) | BCl$_3$ (used as 2 mol dichloroethane solution) | (5 mmols) | 38% |
| 5 (Invention) | ZnCl$_2$ | (5 mmols) | 22% |
| 6 (Comparison) | none | | 0% |

[1] Mol number to 2 mmols of Compound (VI-7a)
[2] Each of CuO and the solution were added to the reaction mixture From Table 3, it can be seen that when the Lewis acid is not added, the reaction does not proceed (No. 6), while by adding CuCl$_2$, BCl$_3$, or ZnCl$_2$, the desired product is obtained (Nos. 1, 4, and 5). Also, the reaction is accelerated by adding an additive such as LiBr (No. 3). Furthermore, under the condition of reacting CuO and HBr in the reaction system of compounds of i), ii) and iii) to form CuBr$_2$ in the system, the reaction proceeds efficiently (No. 2).

EXAMPLE 4

Synthesis of Compound (VI-17)

The compound was prepared by the process as in Example 3 except that acetonitrile was used in place of toluene as the reaction solvent and 0.4 mmol of CuCl$_2$ as the metal salt.

The yield for the product was 38% and the melting point thereof was from 63.5° C. to 66.0° C.

EXAMPLE 5

Synthesis of Compound (VI-5)

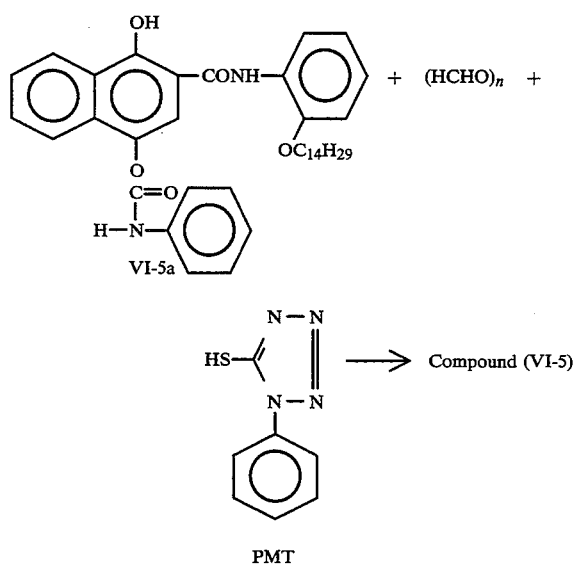

In to a mixture of 2 mmols of Compound (VI-5a), 3 mmols of paraformaldehyde, 3 mmols of PMT, and 1.0 mmol of CuBr$_2$ were added 20 ml of 1,2-dichloroethane and the reaction was carried out for 6 hours at 50° C. Then, the reaction mixture was treated as in Example 2 to provide 0.82 mmol (yield 41%) of Compound (VI-5) having a melting point of from 124.5° C. to 127.0° C.

EXAMPLE 6

Synthesis of Compound VI-14

The compound was prepared by the same manner as in Example 2. The yield thereof was 46% and the melting point thereof was from 108.5° C. to 110.5° C.

EXAMPLE 7

Synthesis of Compound IV-1

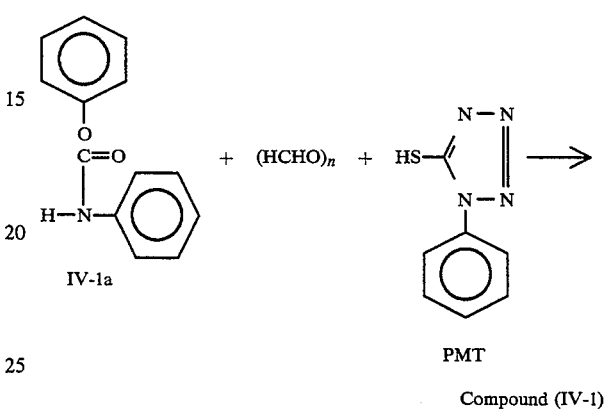

In to a mixture of 10 mmols of Compound (IV-1a), 10 mmols of paraformaldehyde, 10 mmols of PMT, and 0.5 mmol of CuBr$_2$ was added 40 ml of 1,2-dichloroethane and the reaction was carried out for 7 hours at 45° C. By treating the reaction mixture in the same manner as in Example 2 the Compound (IV-1) was obtained at a yield of 63%. The melting point thereof was from 114.5° C. to 116.5° C.

Compound (IV-2) was obtained in the same manner as above except using of Compound (IV-2a) in place of Compound (IV-1a) with a yield of 86%. (Oily product).

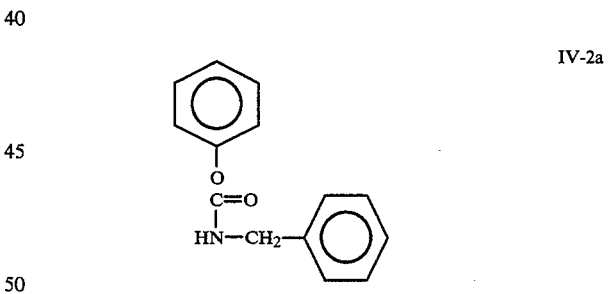

EXAMPLE 8

Synthesis of Compound (VI-7) (Easy isolation method)

A mixture of 0.1 mol of Compound (VI-7a), 0.1 mol of paraformaldehyde, 0.1 mol of BMT, and 0.02 mol of CuBr$_2$ was reacted in 400 ml of toluene for 7 hours at 45° C. Thereafter, the reaction mixture obtained was washed twice with 400 ml of water. The organic layer formed was collected and after adding thereto 100 g of active carbon followed by stirring, the mixture was filtered through a zeolite, and then the toluene solution obtained was concentrated under a reduced pressure. The residue obtained was recrystallized from a mixture of hexane and isopropyl alcohol and recrystallized again with the same solvents to provide Compound (VI-7) at a yield of 65%. The melting point of the product was from 96.0° C. to 97.0° C.

As described above, it has been confirmed that by using the process of the present invention, the compound represented by formula (IV) can be synthesized from the compound shown by formula (I) by one step with a good yield, and a method capable of easily isolating the product.

While the invention has been described in detail and with reference to specific embodiments thereof, it will be apparent to one skilled in the art that various changes and modifications can be made therein without departing from the spirit and scope thereof.

What is claimed is:

1. A process of synthetizing an acetal, which comprises reacting, i) a compound represented by formula (I);

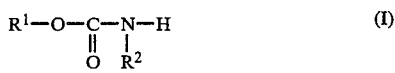

wherein $R^1$ represents an alkyl group, an aryl group, or a heterocyclic group and $R^2$ represents an alkyl group or an aryl group, said groups represented by $R^1$ and $R^2$ may be substituted, ii) at least one compound selected from the group consisting of paraformaldehyde, trioxane and compound represented by formula (II);

wherein $R^3$ and $R^4$ each independently represents a hydrogen atom, an alkyl group, an alkenyl group, an alkinyl group, an alkoxycarbonyl group, an aryloxycarbonyl group, a carbamoyl group, a sulfamoyl group, an aryl group, or a heterocyclic group, said groups represented by $R^3$ and $R^4$ may be substituted, and iii) a compound represented by formula (III);

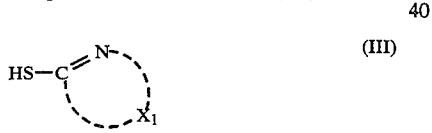

wherein $X_1$ represents a non-metallic atomic group necessary for forming a 5-membered or 6-membered nitrogen atom-containing heterocyclic group which may be condensed with another ring to form a di- or tri-cyclic group, said groups represented by $X_1$ may be substituted, in the presence of at least one of a Lewis acid and a metal salt to synthesize the acetal represented by formula (IV);

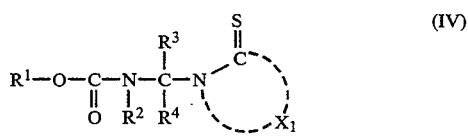

wherein $R^1$, $R^2$, $R^3$, $R^4$, and $X_1$ have the same meaning as those in formula (I), (II) and (III).

2. The process of synthesizing the acetal as claimed in claim 1, wherein the substituent for the substituted groups represented by $R^1$, $R^2$, $R^3$, $R^4$ and $X_1$ is selected from the group consisting of an alkyl group, an aryl group, a carbamoyl group, an alkoxy group, an aryloxy group, an alkylthio group, an arylthio group, an alkoxycarbonyl group, an-aryloxycarbonyl, a nitro group, a cyano group, a halogen atom, a sulfamoyl group, an acylamino group, a sulfonylamino group, and an amino group, and said groups, except a nitro group and a cyano group may be further substituted with at least one of these substituents.

3. The process of synthesizing the acetal as claimed in claim 1, wherein $R^1$ is represented by formula (V);

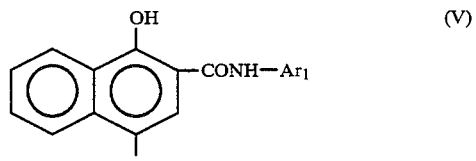

wherein $Ar_1$ represents a substituted or unsubstituted alkyl group or a substituted or unsubstituted aryl group.

4. The process of synthesizing the acetal as claimed in claim 3, wherein the substituent for the substituted groups represented by $Ar_1$ is selected from the group consisting of an alkyl group, an aryl group, a carbamoyl group, an alkoxy group, an aryloxy group, an alkylthio group, an arylthio group, an alkoxycarbonyl group, an aryloxycarbonyl, a nitro group, a cyano group, a halogen atom, a sulfamoyl group, an acylamino group, a sulfonylamino group, and an amino group, and said groups except a nitro group and a cyano group may be further substituted with at least one of these substituents.

5. The process of synthesizing the acetal as claimed in claim 1, wherein the acetal is represented by formula (VI):

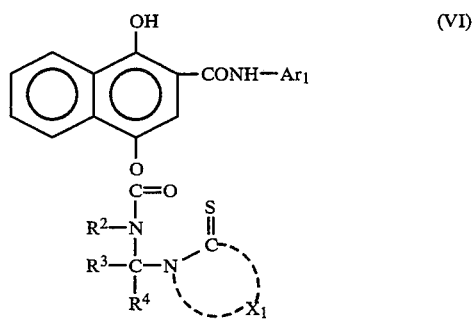

wherein $Ar_1$ represents a substituted or unsubstituted alkyl group or a substituted or unsubstituted aryl group and $R^2$, $R^3$, $R^4$, and $X_1$ each has the same meaning as in formula (IV).

6. The process of synthesizing the acetal as claimed in claim 1, wherein the substituent of the group represented by $X_1$ is selected from the group consisting of an alkyl group, an aryl group, a carbamoyl group, an alkoxy group, an aryloxy group, an alkylthio group, an arylthio group, an alkoxycarbonyl group, an aryloxycarbonyl, a nitro group, a cyano group, a halogen atom, a sulfamoyl group, an acylamino group, a sulfonylamino group, and an amino group, and said group except a nitro group and a cyano group may be further substituted with at least one of these substituents.

7. The process of synthesizing the acetal as claimed in claim 1, wherein the heterocyclic moiety of said compound represented by formula (III) is selected from the group consisting of groups represented by formula (III-1) to (III-8):

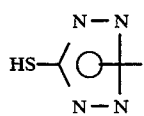
(III-1)

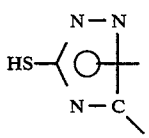
(III-2)

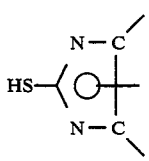
(III-3)

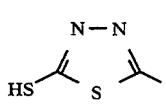
(III-4)

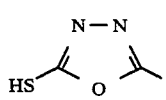
(III-5)

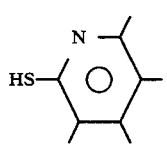
(III-6)

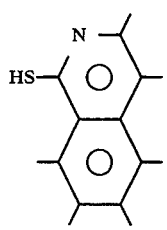
(III-7)

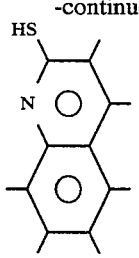
(III-8)

8. The process of synthesizing the acetal as claimed in claim 1, wherein $R^3$ and $R^4$ in formula (II) each represents a hydrogen atom, an alkyl group having from 1 to 6 carbon atoms or a phenyl group.

9. The process of synthesizing the acetal as claimed in claim 1, wherein the compound of ii) is paraformaldehyde.

10. The process of synthesizing the acetal as claimed in claim 1, wherein said at least one of the Lewis acid and the metal salt is selected from the group consisting of trivalent boron compounds, trivalent aluminum compounds, divalent nickel compounds, divalent zinc compounds, tetravalent or heptavalent vanadium compounds, monovalent or divalent silver compounds, iodotrimethylsilane, monovalent or divalent copper compounds, and solid acid catalysts.

11. The process of synthesizing the acetal as claimed in claim 1, wherein the reaction is conducted under the presence of a halogen ion source.

12. The process of synthesizing the acetal as claimed in claim 1, wherein each of the compounds of i), ii) and iii) is used in an equimolar amount.

13. process of synthesizing the acetal as claimed in claim 1, wherein said at least one of Lewis acid and the metal salt is used in a molar amount of from 0.001 times to 10 times the smallest molar amount of the three compounds of i), ii) and iii).

14. The process of synthesizing the acetal as claimed in claim 11, wherein the halogen ion source is used in a molar amount of 0.001 times to 20 times the smallest molar amount of the three compounds of i), ii) and iii).

15. The process of synthesizing the acetal as claimed in claim 1, wherein the metal salt is formed in the reaction system comprising the three compounds of i), ii) and iii) by reacting a metal oxide corresponding to the metal salt with a protonic acid.

16. The process of synthesizing the acetal as claimed in claim 1, wherein the reaction of the three compounds of compounds of i), ii) and iii) is carried out at a temperature of from 0° C. to 150° C.

17. process of synthesizing the acetal as claimed in claim 1, wherein the reaction of the three compounds of compounds of i), ii) and iii) is carried out in a solvent.

18. The process of synthesizing the acetal as claimed in claim 17, wherein the smallest concentration of among the concentrations of compounds i), ii) and iii) is $10^6$ mol/liter.

19. The process of synthesizing the acetal as claimed in claim 1, wherein the reaction of the three compounds of compounds of i), ii) and iii) is carried out at a temperature of from 20° C. to 80° C.

20. The process of synthesizing the acetal as claimed in claim 1, wherein the reaction time of the three compounds of compounds of i), ii) and iii) is in the range of from 30 minutes to 3 days.

* * * * *